United States Patent

Kusch et al.

[11] Patent Number: 6,132,087
[45] Date of Patent: Oct. 17, 2000

[54] MEDICAL APPARATUS HAVING A CARRYING DEVICE FOR AT LEAST ONE COMPONENT

[75] Inventors: Jochen Kusch, Effeltrich; Helmut Richter, Baiersdorf, both of Germany

[73] Assignee: Siemens Aktiengesellschaft, Munich, Germany

[21] Appl. No.: 09/166,682

[22] Filed: Oct. 5, 1998

[30] Foreign Application Priority Data

Oct. 17, 1997 [DE] Germany .............................. 197 46 079

[51] Int. Cl.⁷ ...................................................... H05G 1/02
[52] U.S. Cl. ........................................... 378/197; 378/198
[58] Field of Search ..................................... 378/195–198

[56] References Cited

U.S. PATENT DOCUMENTS

Re. 34,943  5/1995  Van Endschot et al. .
5,425,068  6/1995  Schaefer et al. .
5,426,683  6/1995  O'Farrell et al. ........................ 378/197
5,469,492  11/1995  Burbury et al. ........................ 378/197

FOREIGN PATENT DOCUMENTS 40 03 350  4/1991  Germany .

Primary Examiner—Craig E. Church
Attorney, Agent, or Firm—Hill & Simpson

[57] ABSTRACT

A medical apparatus has a carrying device for at least one component, wherein the carrying device is adjustable relative to a holding mechanism and is formed of plastic. Rollers at least partly formed of plastic are provided for the adjustment of the carrying device relative to the holding mechanism, the carrying device being seated on these rollers and these rollers running directly on a plastic surface of the carrying device.

18 Claims, 3 Drawing Sheets

MEDICAL APPARATUS HAVING A CARRYING DEVICE FOR AT LEAST ONE COMPONENT

BACKGROUND OF THE INVENTION

1. Field of the Invention

The present invention is directed to a medical apparatus of the type having a carrying device for at least one component, the carrying device being adjustable relative to a holding mechanism.

2. Description of the Prior Art

German PS 42 14 858, corresponding to U.S. Pat. No. 5,425,068, discloses a medical apparatus of the type initially described. The medical apparatus is an X-ray device with carrying device in the form of a C-arm carrying an X-ray source and an X-ray image intensifier, this carrying device being mounted so as to be adjustable along its circumference in a holding mechanism. The C-arm is formed of plastic and has two guide rails of metal at both sides in the region of the greatest expanse of its cross-section, rollers for the adjustment of the C-arm relative to the holding mechanism running on these rails. The guide rails of metal are required in order to keep the rolling friction drag and the wear low. The presence of the guide rails is also required in order to absorb the forces acting on the C-arm due to the rollers of the holding mechanism.

Such a C-arm is usually weight-compensated in order to enable manual adjustment of the C-arm relative to the holding mechanism. The X-ray source, the X-ray image intensifier and the C-arm are thereby balanced relative to the pivot point of the C-arm by appropriate attachment of compensation weights to, for example, the C-arm. A disadvantage of this known C-arm is that the beam path of the central ray of an X-ray beam emanating from the X-ray source does not proceed through the pivot point of the C-arm, i.e. the C-arm does not have an isocenter. In a radiological examination of a subject with the assistance of the known C-arm X-ray device wherein the subject is positioned in the beam path of the central ray of an X-ray beam emanating from the X-ray source, the subject, given a change of the projection direction due to adjustment of the C-arm along its circumference relative to the subject, is then only partially in the beam path of the central ray of the X-ray beam or not at all, causing the X-ray image of the subject under examination, that is usually displayed on the picture screen of a viewing means, to migrate across the picture screen or to be entirely out of the picture screen. The migration of the subject across or out of the picture screen therefore requires a repositioning of the C-arm relative to the subject, causing the medical examination to be lengthened and causing the patient to be subjected to an additional radiation exposure.

U.S. Pat. No. Re. 34,943 discloses an X-ray device with a C-arm formed of an aluminum alloy that carries an X-ray source, an adjustable X-ray image intensifier and an adjustable balancing weight, wherein the beam path of the central ray of an X-ray beam emanating from the X-ray source proceeds through the pivot point of the C-arm. A disadvantage is that this X-ray device is not suitable for mobile use since it would fall over forwards due to the weight of the X-ray source, the X-ray image intensifier, the balancing weight and the dead weight of the C-arm, all of which would have to be arranged at an apparatus cart of the X-ray device if it were to be made mobile. Counterweights that could compensate for the heavy metal arc, the X-ray source, the X-ray image intensifier and the balancing weight could not be employed for weight reasons, since the mobility and the positionability of the X-ray device would be substantially restricted due to the heavy weight which would be required.

Even given an embodiment of the C-arm according to German PS 42 14 858, the X-ray device would still exhibit such a high dead weight that it would not be suitable for mobile use.

Although German PS 40 03 350 discloses a mobile C-arm X-ray device whose C-arm seated in a holding mechanism comprises an isocenter, the C-arm is not provided with balancing weights such that the C-bend could be unproblematically manually adjusted in the holding mechanism.

SUMMARY OF THE INVENTION

An object of the present invention is to provide a medical apparatus of the type initially described wherein the carrying device exhibits an especially low dead weight in order to reduce the weight of the medical apparatus. The precondition for the mobile use of the medical apparatus with a weight-compensated, isocentrically adjustable carrying mechanism is created in this way.

This object is inventively achieved in a medical apparatus with a carrying device for at least one component that is adjustable relative to a holding mechanism and is formed of plastic, wherein rollers formed at least partly of plastic are provided for the adjustment of the carrying device relative to the holding mechanism, the carrying device being seated on these rollers and these rollers running directly on a plastic surface of the carrying device. The carrying device exhibits an especially low dead weight because the carrying device is formed virtually completely of plastic, preferably plastic with carbon fibers. The carrying device is directly seated on rollers of plastic that inventively run directly on a plastic surface of the carrying device, with the bearing of the carrying device on the plastic rollers being implemented such that weight-increasing guide rails, for example metal rails as disclosed in German PS 42 14 858 for reducing the rolling friction drag of the rollers, wear and for absorbing the forces acting on the carrying device due to the rollers, can be foregone. By contrast to the carrying device disclosed in German PS 42 14 858, the inventive carrying device has neither a weight-increasing formed member nor an extruded aluminum profile or metallic cross-bracing that serve in the known apparatus for shaping and stabilizing the carrying device. On the contrary, the manufacture and shaping of the carrying device of the invention preferably ensues by the use assistance of negative molds wherein the plastic is pressed and hardened under pressure, and possibly with the application of heat.

The inventive embodiment of the carrying device of plastic creates the pre-conditions for making the medical apparatus mobile, in an embodiment of the invention. Since the carrying device inherently exhibits a low dead weight, there is the possibility of attaching counterweights to the medical apparatus for the stabilization of the carrying device, provided with components and possibly balancing weights, but the inventive medical apparatus still exhibits such an overall weight that its mobility and positionability are not restricted.

In an embodiment of the invention the carrying device exhibits different cross-sectional geometries along its extent, the cross-sectional geometries preferably continuously (smoothly) merging into one another. The cross-sectional geometries are thereby correspondingly adapted to the component or components arranged at the carrying device, with a stabilization of the carrying device being thereby effected by virtue of the torsion produced in the carrying device by the components being counteracted or opposed. The cross-sectional geometries adapted to the stressing of the carrying device by the components arranged at the carrying device thus allow additional attachment parts to be forgone such as, for example, metal cross-bracing rails for stabilizing the carrying device.

In a version of the invention the carrying device provided with the components is weight-compensated by appropriate attachment of weights for allowing manual adjustment of the carrying device. In this way, the carrying device can be simply and quickly manually adjusted (positioned) relative to the holding mechanism, thereby allowing expensive, electrically operated units such as, for example, electric motors for the adjustment of the carrying device, to be foregone.

In a preferred embodiment of the invention, the carrying device is in the shape of a C-arc so that the component such that the component or components carried by the carrying device does/do not project outwardly beyond the C-arc profile of the carrying device i.e., the component or components is/are fully disposed with the circumference of the C-arc. The pre-conditions are thus created that, according to a further version of the invention, the carrying device has a range of adjustment of at least 190° along its circumference in the holding mechanism. The diameter of the C-arc carrying device to achieve this result must be larger than the known C-arc carrying devices, but this is made feasible by the light-weight nature of the inventive device. As a result, the accessibility to the patient is considerably improved without restricting the mobility and the positionability of the medical apparatus due to an increase in weight.

In another embodiment of the invention the carrying device carries an X-ray source and an X-ray receiver opposite one another, and the pivot point of the carrying device lies in the beam path of the central ray of an X-ray beam emanating from the X-ray source. The medical apparatus thus has an isocenter, so that a subject once positioned in the isocenter always advantageously remains in the isocenter given adjustment of the C-arc carrying device along its circumference in the holding mechanism relative to the subject, and the image of the subject thus does not undesirably migrate across the picture screen of the viewing means given presentation of the subject on such a picture screen.

DESCRIPTION OF THE PREFERRED EMBODIMENTS

Figure 1:
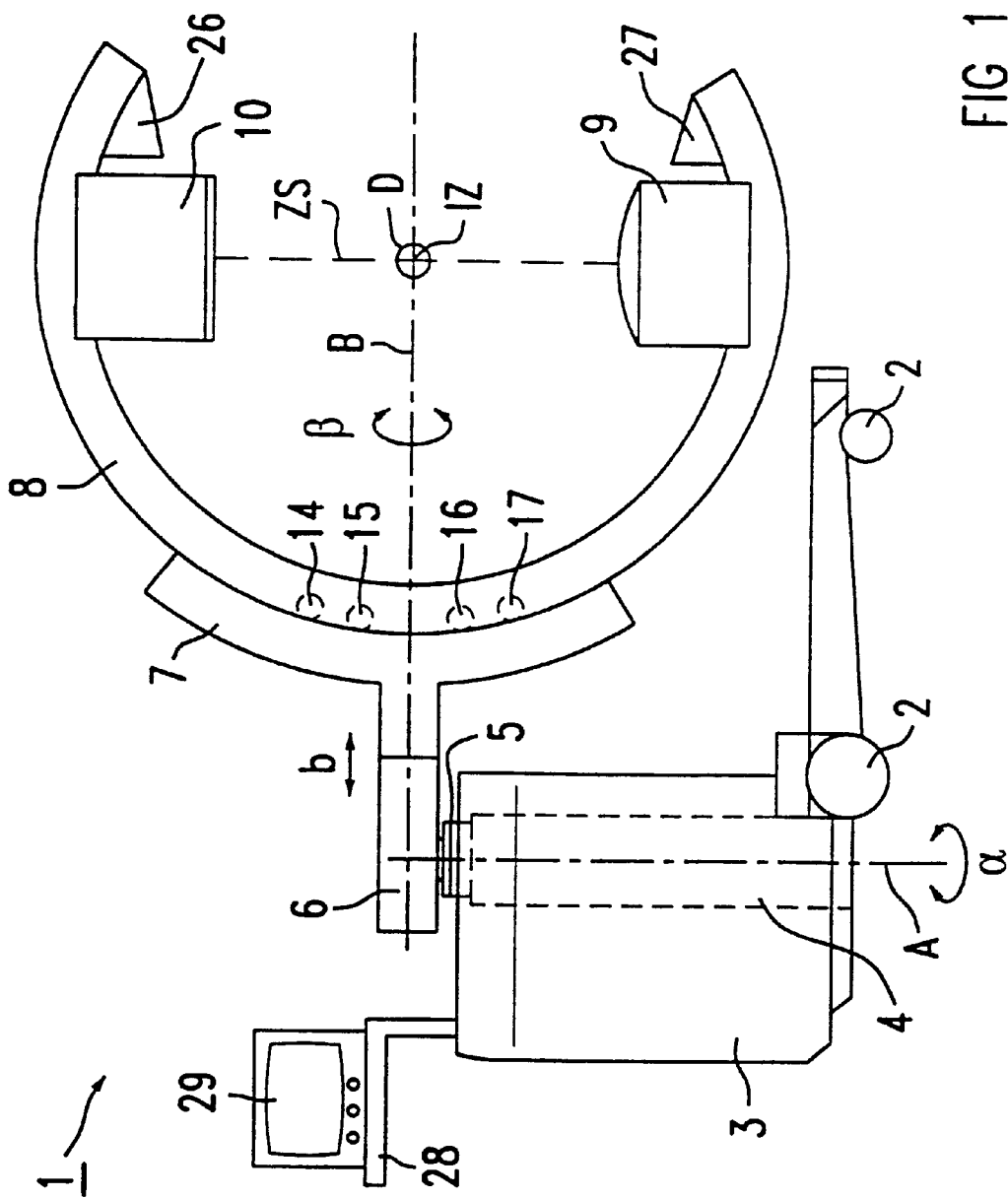
FIG. 1 is a side view of an inventive medical apparatus.

The medical apparatus in the present exemplary embodiment is a C-arm X-ray apparatus 1 with an apparatus cart 3 movable on wheels 2. The C-arm X-ray apparatus 1 has a lifting mechanism 4 (only schematically indicated in FIG. 1) with a column 5 having a longitudinal axis A around which the column 5 is rotatable in the direction of the double arrow a. A holder part 6 is arranged at the column 5, a holding mechanism 7 for bearing a carrying device fashioned as C-arm 8 being in turn arranged at the holder part 6. Lying opposite one another, the C-arm 8 carries an X-ray source 9 and an X-ray image intensifier 10 that are arranged relative to one another so that a central ray ZS of a X-ray beam emanating from the X-ray source 9 strikes the input luminescent screen of the X-ray image intensifier 10 approximately centrally. In a known way, the holding mechanism 7 is seated at the holder part 6 so as to be rotatable around a common axis B of the holder part 6 and the holding mechanism 7 (see the double arrow β, angulation) and is displaceable in the direction of the axis B (see the double arrow b). The C-arm 8, which is connected to the lifting mechanism 4 via the holding mechanism 7 and the holder part 6, is vertically adjustable relative to the apparatus cart 3 with the assistance of the lifting mechanism 4.

Figure 2:
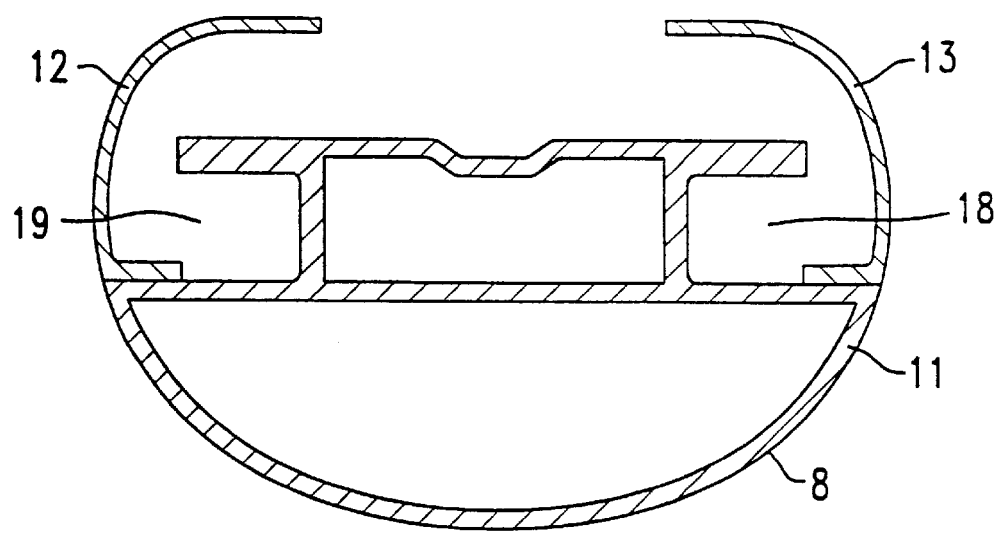
FIG. 2 shows the cross-sectional geometry of a C-arc carrying device in the apparatus of FIG. 1.

The C-arm 8 of the C-arm X-ray apparatus 1 of FIG. 1 shown in crossection in FIG. 2 has a base part 1 1 and two attachment parts 12, 13 that are screwed to the base part 11 in a way not shown, for example with plastic screws. The base part 11 as well as the attachment parts 12, 13 are likewise fashioned of plastic, for example carbon fiber plastic. The C-arm 8 exhibiting generally constant cross-sectional geometry is seated with generally structurally identical rollers (the rollers 14 through 17 are visible in FIG. 1 in the schematically indicated way) in the holding mechanism 7, this adjustment being in the direction of the double arrow a along its circumference. The C-arm has recesses 18, 19 wherein the rollers run directly on the plastic surface of the C-arm 8 given adjustment of the C-bend 8 relative to the holding mechanism 7.

Figure 3:
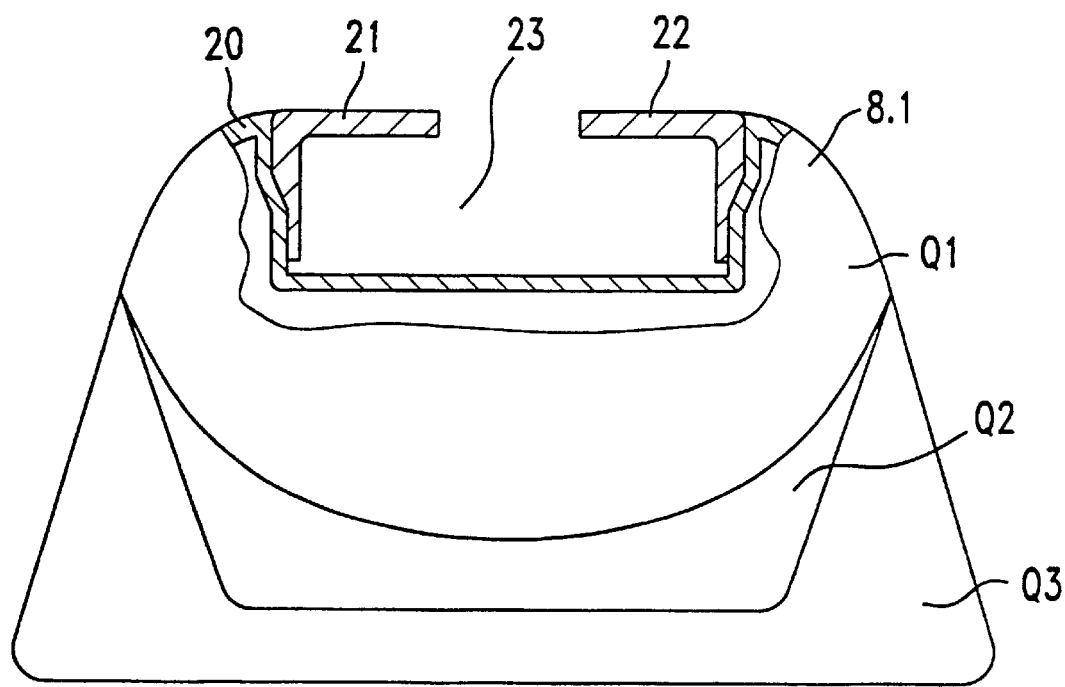
FIG. 3 is a superimposed view showing the cross-sectional geometries of a further C-arc carrying device of the invention.

FIG. 3 shows the cross-sectional geometries of a further embodiment of a C-arm 8.1 that is seated in the holding mechanism 7 instead of the C-arm 8 and can be provided with the X-ray source 9 and the X-ray image intensifier in a way analogous to the C-arm 8. The C-arm 8.1 has different cross-sectional geometries along its extent that preferably continuously merge into one another. In a superimposed illustration, FIG. 3 shows the various cross-sectional geometries of the C-arm 8.1. The C-arm 8.1 has the cross-sectional geometry Q1 in the region of its middle, the cross-sectional geometry Q2 in the region of the X-ray source 9 and the cross-sectional geometry Q3 in the region of the X-ray image intensifier 10. The cross-sectional geometries of the C-arm 8.1 are implemented such that the torsion produced in the C-arm 8.1 by the X-ray source 9 and the X-ray image intensifier 10 is counteracted, of the C-arm 8.1 being made stable as a result. In this way, no further attachment parts are required for the stabilization of the C-arm 8.1. Analogous to the C-arm 8, the C-arm 8.1 has a base part 20 and two attachment parts 21, 22 that, for example, are screwed to the base part 20. The base part 20 and the attachment parts 21, 22 are fashioned completely of plastic. Together with the attachment parts 21, 22, the base part 20 forms a U-shaped recess 23 in which the rollers of the holding mechanism 7 for bearing the C-arm 8.1 run. As in the case of the C-arm 8, the rollers of the holding mechanism 7 in the C-arm 8.1 also run directly on the plastic surface of the C-arm 8.1.

Thus any and all attachment parts of metal, whether for stabilization, for shaping or for absorbing forces acting on the C-arms 8, 8.1 during the adjustment, can be foregone in the C-arms 8 and 8.1, so that the dead weight of the C-arm is substantially reduced compared to known C-arms.

Figure 4:
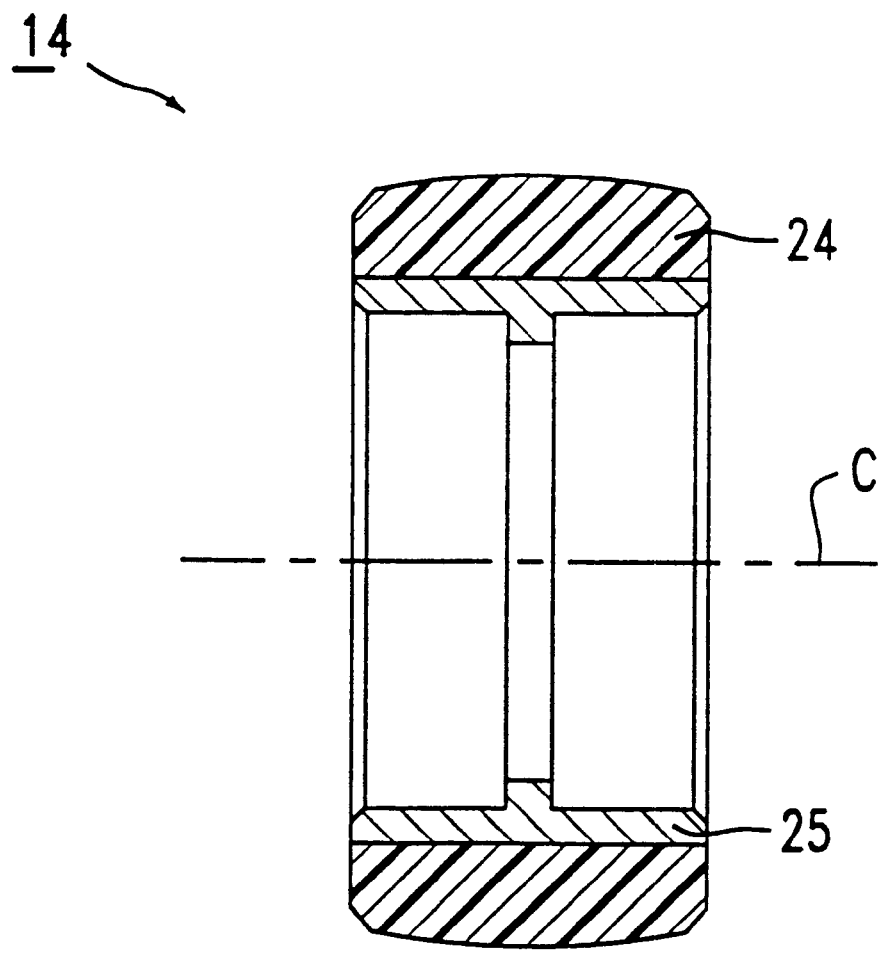
FIG. 4 shows a roller of the medical apparatus of FIG. 1.

In order to keep the rolling friction drag and the wear as a consequence of the rolling of the rollers of the holding mechanism 7 on the plastic surfaces of the C-arm 8 or 8.1 low, the rollers of the holding mechanism 7 are formed at least partly of plastic. FIG. 4 shows the roller 14 of the holding mechanism 7 in sectional form by way of example. The roller 14 has a core roller 25 formed, for example, of aluminum provided with a plastic coating 24 that, given appropriate bearing with, for example, ball bearings (not shown in the Figures), is rotatable around an axis C. Like the C-arm 8 or 8.1, the plastic coating 24 is preferably formed of plastic with carbon fibers. The surfaces of the plastic coatings of the rollers as well as the surfaces of the C-arm 8 or 8.1 on which the rollers run are fashioned such that they exhibit surface roughnesses and hardnesses comparable to metallic surfaces. It is thus assured that the wear of the rollers of plastic and of the plastic surfaces of the C-arm 8 or 8.1 on which the rollers run is not increased. The rollers need not necessarily have a core roller 25 of aluminum, but can be completely formed of plastic.

The C-arm 8 of FIG. 1 provided with the X-ray source 9 and the X-ray image intensifier 10 is also provided with weights 26, 27 so that it is weight compensated for manual adjustability, whereby the C-arm 8, the X-ray source 9 and the X-ray image intensifier 10 are in balance relative to the pivot point D of the C-arm 8. In this way, the C-arm 8 can be simply and easily manually adjusted along its circumference in the holding mechanism 7. The pivot point D of the C-arm thereby lies in the beam path of the central ray ZS of a X-ray beam emanating from the X-ray source 9, the pivot point D being the intersection of the axis B with the central ray ZS. The position of the pivot point D in the beam path of the central ray ZS causes the movements of the C-bend 8 to ensue isocentrically, so that a subject once positioned in the isocenter IZ that, for example, can be displayed in the form of an X-ray image on the picture screen of a monitor 29 arranged at a holder 28 of the C-arm X-ray apparatus, 1 does not migrate in or out of the picture screen of the monitor 29 given an arbitrary adjustment of the C-arm 8 along its circumference (orbital motion). A repositioning of the C-arm 8 relative to a subject to be examined, which involves as additional radiation dose for the subject, is avoided in this way.

The low dead weight of the C-arm 8 formed of plastic also makes it possible to implement the C-arm 8 with such a large diameter that it embraces the X-ray source 9 and the X-ray image intensifier 10 so that the X-ray source 9 and the X-ray image intensifier 10 do not project outwardly beyond the C-arc profile of the C-arm 8. In this way, the X-ray source 9 and the X-ray image intensifier 10 do not impede the adjustment motion of the C-bend 8 relative to the holding mechanism 7 or limit it to a specific range, so that the C-arm 8 has a range of adjustment of at least 190° along its circumference. Since the C-arm 8 has a significantly larger diameter compared to known C-arms, the accessibility to a subject to be examined is also noticeably improved.

The C-arm of the C-arm X-ray apparatus 1, moreover, need not necessarily have the cross-sectional geometries shown in FIGS. 2 and 3 but can be differently fashioned, the important factor being that the C-arm is able to be completely fashioned of plastic.

Further, the number of rollers of the holding mechanism provided for the bearing of the C-arm can deviate from the number indicated in the present exemplary embodiment.

In a way that is not shown, moreover, counterweights for the C-arm 8 provided with the X-ray source 9, the X-ray image intensifier 10 and the weights 26, 27 can be present at the apparatus cart 3 for the stabilization of the C-arm X-ray apparatus 1.

The invention was explained above with reference to the example of a mobile C-arm X-ray apparatus 1. The employment of the carrying device, however, is not limited to utilization in mobile C-bend X-ray apparatus but can also be utilized in a stationary X-ray apparatus or in other medical equipment, for example in lithotriptors, for carrying a shock wave source.

Although modifications and changes may be suggested by those skilled in the art, it is the intention of the inventor to embody within the patent warranted hereon all changes and modifications as reasonably and properly come within the scope of his contribution to the art.

We claim as our invention:

1. A medical X-ray apparatus comprising:
   a C-arm;
   a holding mechanism for supporting said C-arm;
   said C-arm mechanically engaging said holding mechanism, and carrying at least one X-ray component;
   said C-arm being comprised of plastic and having a plastic surface;
   a plurality of rollers comprised at least partially of plastic and having a plastic exterior coating, said rollers being disposed inside said C-arm and being operable to run with said plastic coating directly on said plastic surface of said C-arm; and
   means for adjusting a position of said C-arm relative to said holding mechanism.

2. A medical X-ray apparatus as claimed in claim 1 further comprising a mobile cart on which said holding mechanism is mounted.

3. A medical X-ray apparatus as claimed in claim 1 wherein said C-arm is adjustable relative to said holding mechanism along an adjustment direction, and wherein said C-arm has a plurality of different cross-sectional geometries, substantially perpendicular to said adjustment direction, along said adjustment direction.

4. A medical X-ray apparatus as claimed in claim 1 further comprising a weight carried by said C-arm for compensating for a weight of said at least one component.

5. A medical X-ray apparatus as claimed in claim 1 wherein said a C-arm has a C-arm profile, and wherein said at least one X-ray component is mounted on said C-arm so that said at least one X-ray component does not project outwardly beyond said C-arm profile.

6. A medical X-ray apparatus as claimed in claim 5 wherein said C-arm has a circumference, and wherein said C-arm is adjustable along said circumference in said holding mechanism through at least 190°.

7. A medical X-ray apparatus as claimed in claim 5 further comprising an X-ray source and an X-ray image intensifier disposed opposite each other on said C-arm, said X-ray source emitting an X-ray beam having a central ray, and wherein said C-arm has a pivot point disposed in a path of said central ray.

8. A medical X-ray apparatus as claimed in claim 7 wherein said pivot point comprises an isocenter of said C-arm.

9. A medical X-ray apparatus comprising:
   a C-arm having a circumference and comprised of plastic, carrying said X-ray source and an X-ray receiver opposite each other, said C-arm having different cross-sectional geometries along said circumference including a middle region with a first cross-sectional geometry, a region for arranging said x-ray source with a second cross-sectional geometry and a region for arranging said X-ray receiver with a third cross-sectional geometry, and having a C-arm profile, said X-ray source and said X-ray receiver being mounted on said C-arm so that said X-ray source and said X-ray receiver do not project outwardly beyond said C-arm profile;

a holding mechanism for supporting said C-arm, said C-arm mechanically engaging said holding mechanism; and means for adjusting a position of said C-arm relative to said holding mechanism along said circumference of said C-arm.

10. A medical x-ray apparatus as claimed in claim 9 further comprising a mobile cart on which said holding mechanism is mounted.

11. A medical X-ray apparatus as claimed in claim 9 further comprising a weight carried by said C-arm for compensating for a weight of said at least one component.

12. A medical X-ray apparatus as claimed in claim 9 wherein said C-arm has a circumference, and wherein said C-arm is adjustable along said circumference in said holding mechanism through at least 190°.

13. A medical X-ray apparatus as claimed in claim 9 wherein said X-ray source emits an X-ray beam having a central ray and wherein said holding mechanism pivots said C-arm around a pivot point disposed in a path of said central ray.

14. A medical X-ray apparatus as claimed in claim 13 wherein said pivot point comprises an isocenter of said C-arm.

15. A medical X-ray apparatus comprising:

an X-ray source and an X-ray receiver;

a holding mechanism;

a C-arm carrying said X-ray source and said X-ray receiver and mechanically engaging said holding mechanism, said C-arm having a circumference and a C-arm profile and being comprised of plastic;

means for adjusting a position of said C-arm relative to said holding mechanism;

said X-ray source and said X-ray receiver being mounted on said C-arm so that said X-ray source and said X-ray receiver do not project outwardly beyond said C-arm profile said C-arm being isocentrically adjustable along said circumference in said holding mechanism through at least 190°, and weights connected to said C-arm so that said C-arm is weight-compensated for manual adjustability; and a mobile cart on which said holding mechanism is attached, said mobile cart having counterweights for stabilizing a combination of said mobile cart and said C-arm with said X-ray source and X-ray receiver.

16. A medical X-ray apparatus as claimed in claim 15 wherein said C-arm is adjustable relative to said holding mechanism along an adjustment direction, and wherein said C-arm has a plurality of different cross-sectional geometries, substantially perpendicular to said adjustment direction, along said adjustment direction.

17. A medical X-ray apparatus as claimed in claim 15 wherein said X-ray source emits an X-ray beam having a central ray and wherein said holding mechanism pivots said C-arm around a pivot point disposed in a path of said central ray.

18. A medical X-ray apparatus as claimed in claim 17 wherein said pivot point comprises an isocenter of said C-arm.

* * * * *